United States Patent [19]

Lestini

[11] Patent Number: 5,086,757

[45] Date of Patent: Feb. 11, 1992

[54] THREE-POINT CERVICAL FIXATION DEVICE

[76] Inventor: William F. Lestini, 3531 39th St., NW., Condo B500, Washington, D.C. 20016

[21] Appl. No.: 620,074

[22] Filed: Nov. 30, 1990

[51] Int. Cl.⁵ .......................... A61F 5/08; A61F 5/02; A61F 5/04

[52] U.S. Cl. ...................................... 602/17; 602/18; 602/19

[58] Field of Search ............ 128/87 B, 85, 87 R, 128/75, 76 R, 84 C, 84 R, 78, 89 R

[56] References Cited

U.S. PATENT DOCUMENTS

| | | | |
|---|---|---|---|
| 30,601 | 11/1860 | Wright | 128/78 |
| 443,764 | 12/1890 | Hilliard | 128/78 |
| 1,301,276 | 4/1919 | Kroetz | 128/75 |
| 1,803,556 | 5/1931 | Nugent | 128/75 |
| 2,835,247 | 5/1958 | Stabholc | 128/78 |
| 3,336,922 | 8/1967 | Taylor | 128/75 |
| 3,667,457 | 6/1972 | Zumaglini | 128/75 |
| 3,923,046 | 12/1975 | Heifetz | 128/75 |
| 3,926,182 | 12/1975 | Stabholz | 128/78 |
| 3,957,040 | 5/1976 | Calabrese | 128/75 |
| 4,541,421 | 9/1985 | Iverson et al. | 128/87 B |
| 4,559,933 | 12/1985 | Batard | 128/78 |
| 4,620,530 | 11/1986 | Lanier et al. | 128/75 |
| 4,632,099 | 12/1986 | Mollo | 128/87 B |
| 4,667,660 | 5/1987 | Eingorn | 128/75 |
| 4,735,196 | 4/1988 | Krag | 128/75 |
| 4,765,317 | 8/1988 | Eastman et al. | 128/75 |
| 4,807,605 | 2/1989 | Mattingly | 128/75 |
| 4,913,135 | 4/1990 | Mattingly | 128/75 |

Primary Examiner—Robert A. Hafer
Assistant Examiner—Michael Brown
Attorney, Agent, or Firm—Laubscher, Presta & Laubscher

[57] ABSTRACT

A three-point cervical fixation device for a human patient, having a vertical support device extending substantially parallel to the patient's spine, the support having upper and lower ends adjacent the head and torso of the patient, respectively. The upper end of the support means is connected with the patient's head by a first connecting device, and a second connecting device connects a lower portion of the support device with the torso of the patient. A force-applying device connected with the support applies a force to the patient intermediate the first and the second connecting devices in a direction generally away from the support, thereby to stabilize the patient's spine.

8 Claims, 1 Drawing Sheet

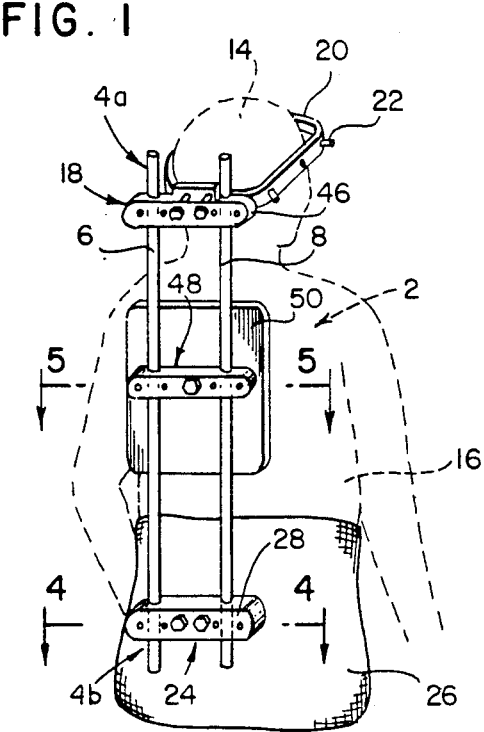
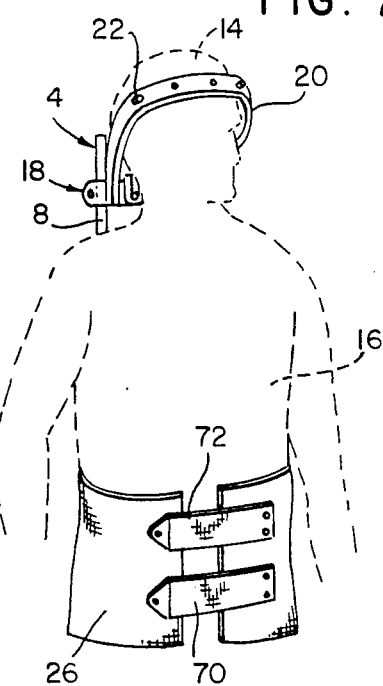
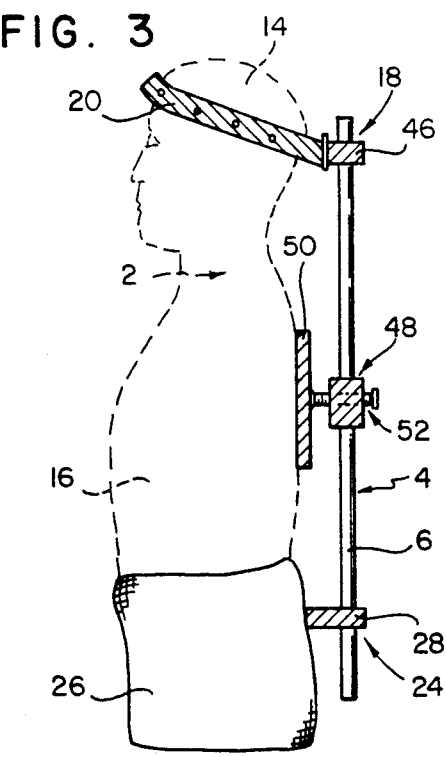
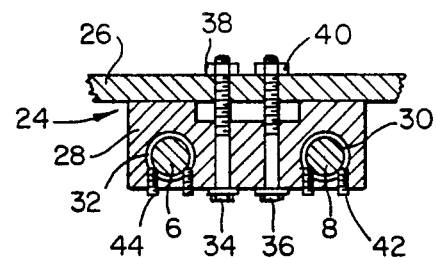
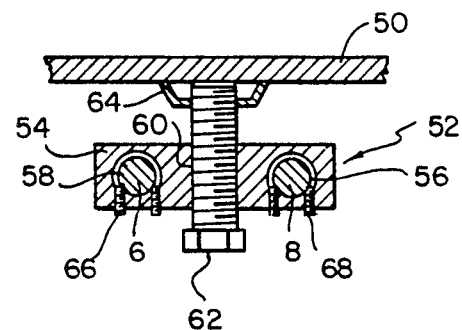

THREE-POINT CERVICAL FIXATION DEVICE

BACKGROUND OF THE INVENTION

1. FIELD OF THE INVENTION

The present invention relates to orthopedic braces for humans, and more particularly to braces for use following injuries involving trauma to the cervical region of the spine.

2. BRIEF DESCRIPTION OF THE PRIOR ART

The non-operative treatment of applying a brace to immobilize the damaged region of the spine during rehabilitation has proven to be the preferred method of treatment for many cervical injuries. Therefore, a need has been created for a reliable and economical device for use in the treatment of cervical spine fractures and cervical instabilities.

Various cervical fixation devices are known in the patented prior art as evidenced by the U.S. Patents to Iverson et al U.S. Pat. No. 4,541,421 and Lanier et al U.S. Pat. No. 4,620,530.

The patent to Iverson et al discloses a halo fixation device for fixation of a head about an orthopedic jacket. The device uses four rods having the lower ends of the rods connected to a jacket worn about the body of a patient. The upper ends of the rods are connected with a halo ring secured to the head of a patient. The patent to Lanier et al U.S. Pat. No. 4,620,530 discloses a halo traction brace which uses a halo ring support assembly connected with a torso-mounted vest.

While the prior cervical devices work satisfactorily in some instances, they do not provide the necessary means for resisting against cervical displacing forces common to such injuries. In particular, the prior art devices do not provide the necessary resistance to displacing forces when used to treat lower cervical fracture-dislocations. As a result, often the treatment of lower cervical instabilities requires surgical stabilization due to the inadequate fixation provided by the prior art devices.

SUMMARY OF THE INVENTION

The present invention was developed to address brace which employs three point fixation to actively resist against cervical displacing forces common to such injuries.

Accordingly, it is a primary object of the present invention to provide a three-point cervical fixation device for a human patient, comprising vertical support means extending substantially parallel to the patient's spine, first means for connecting the upper end of the support means with the patient's head, second means for connecting a lower portion of the support means with the torso of the patient, and force-applying means connected with the support means for applying a force to the patient intermediate the first and second connecting means in a direction generally away from the support means, thereby to immobilize the patient's spine. A more specific object of the present invention, is to provide a cervical fixation device wherein the force-applying means includes a pad adapted to engage the patient's torso between the first and second connecting means, and means adjustably connecting the pad with the support means for displacement in a direction generally normal to the support means, thereby to apply a desired force to a specific location on the patient's spine, preferably at the apex of the thoracic spine region.

According to a more particular object of the present invention, the second connection means includes a corset worn adjacent the lumbar and sacral regions of the patient's spine.

A further object of the invention is to provide a cervical fixation device having a resilient vertical support means to which the first and second connecting means are connected, said force-applying means being operable to cause the cervical fixation device to have a flexed condition, and thereby actively resist cervical displacing forces, such as anterior forces.

DESCRIPTION OF THE FIGURES

Other objects and advantages of the subject invention will become apparent from the study of the following specification when viewed in the light of the accompanying drawings, in which:

FIG. 1 is a rear perspective view of the cervical fixation device as worn by a patient;

FIG. 2 is a front perspective view of the apparatus of FIG. 1;

FIG. 3 is a side view of the apparatus of FIG. 1;

FIG. 4 is a sectional view taken along line 4—4 of FIG. 1; and

FIG. 5 is a sectional view of the force-applying means taken along line 5—5 of FIG. 1.

DETAILED DESCRIPTION

Referring first more particularly to FIG. 1, the three-point cervical fixation device of the present invention is shown as mounted on a patient 2. The device includes vertical support means 4 including a pair of spaced parallel vertical resilient rods 6 and 8. The support means 4 has an upper end 4a and a lower end 4b adjacent the patient's head 14 and torso 16, respectively. First connecting means 18 connect the upper end 10 of the support means 4 with the patient's head 14. The first connecting means 18 includes a halo fixation ring 20 having a plurality of skull pins 22 for attaching the ring to a patient's skull. Although the halo ring 20 is the preferred device for connecting the patient's head 14 with the support means 4, any other means, such as a chin-type connection means, which would securely connect the patient's head 14 with the support means 4, could be used with the present invention.

Second connecting means 24 connect the lower portion of the support means 4 with the patient's torso 16. The second connecting means 24 includes a corset 26 fastened around the lumbar and sacral regions of the patient's spine, and the support means 4 is connected with the second connecting means 24 adjacent the sacral region of the patient's spine.

As shown in FIG. 4, the second connecting means 24 includes a horizontal bridging member 28 extending between the vertical support rods 6 and 8. The bridging member 28 contains holes 32 and 30 for receiving the vertical supports rods 6 and 8, respectively. The bridging member 28 is connected with the corset 26 by bolts 34 and 36 passing through the bridging member 28 and the corset 26 and anchored by nuts 38 and 40, respectively. The holes 32 and 30 enable the second connecting means 24 to be adjusted in the upper and lower directions of the rods 6 and 8, respectively. Set screws 44 and 42 are provided in the bridging member 28 for locking the second connecting means 24 in a desired position on the support means 4, thereby to enable the device to be adjusted for use on a variety of patients. The first connecting means 18 includes a similar bridging member 46, shown in FIG. 1, thereby to enable the first connecting means 18 to also be adjustable in the upper and lower directions of the support means 4.

As shown in FIG. 1, a force-applying means 48 is connected with the support means 4 for applying a force to the patient intermediate the first and second connecting means, 18 and 24, respectively, in a direction generally away from the support means 4, thereby to provide a third point of fixation for stabilizing the patient's spine. This third point of fixation stabilizes the patient's spine by defining an extension moment which actively resists any anterior displacing forces present in the spine.

Referring now to FIG. 3, the force-applying means 48 includes a pad 50 adapted to engage the patient's torso 16 between the first 18 and second 24 connecting means, and means 52 adjustably connecting the pad 50 with the support means 4 for displacement in a direction generally normal to the support means 4, thereby to apply a desired force to a specific location on the patient's spine. Preferably the pad is centered at the apex of the thoracic spine region of the patient, thereby to allow the force-applying means 48 to act on the apex of the thoracic spine region. The pad 50 is constructed to allow the force exerted by the force-applying means 48 to be evenly distributed on the patient by the pad 50, thereby minimizing any discomfort for the patient. Preferably, the support means 4 is slightly resilient, thereby to allow the support means 4 to bend slightly upon application of force on the patient by the force-applying means 48, thereby to enable the device to stabilize the patient's spine by actively resisting any anterior displacing forces present in the patient's spine.

As shown in FIG. 5, the force-applying means comprises adjustable connecting means 52 includes a horizontal bridging member 54 extending between the rods 6 and 8 of the support means 4. The bridging member 54 contains holes 56 and 58 for receiving the rods 6 and 8, respectively. The bridging member contains a threaded bore 60, and an adjusting screw 62 threadably mounted within the bore 60 and terminating at one end adjacent the pad 50. A connector 64 is secured to the pad 50 for connecting the pad 50 with the screw 62, thereby enabling the pad 50 to be adjusted in a direction generally normal to the support means 4. Set screws 66 and 68 are provided in the bridging member 54 for locking the force-applying means 4, thereby enabling the force-applying means 48 to be adjustable in the upper and lower directions relative to the support means 4.

Referring now to FIG. 2, there is shown the corset 26 fastened around the torso 16 of the patient by belts 70 and 72. The first connecting means 18 connected with support means 4, the first connecting means 18 having the halo fixation ring 20 secured to the patient's head 14 be the skull pins 22. As shown in FIG. 2, the chest area of the patient is free from any constriction so that the device does not interfere with the patient's respiratory functions, minimizes patient discomfort, and allows ready emergency access to the patient's chest.

While in accordance with the provisions of the Patent Statute the preferred forms and embodiments have been illustrated and described, it will be apparent to those of ordinary skill in the art that various changes and modifications may be made without deviating from the inventive concepts set forth above.

What is claimed is:

1. A three-point cervical fixation device for a human patient, comprising:
    (a) vertical support means extending substantially parallel to the patient's spine, said support means having upper and lower ends adjacent the head and torso of a patient, respectively;
    (b) first means for connecting said support means upper end with the patient's head;
    (c) second means for connecting a lower portion of said support means adjacent the sacral region of the patient's spine; and
    (d) force-applying means connected with said support means or applying a force to the apex of the thoracic region of the patient's spine intermediate said first and second connecting means in a horizontal direction generally away from said support means, thereby to stabilize the cervical region of the patient's spine.

2. Apparatus as defined as claim 1, wherein said first connecting means includes a halo fixation ring, and a plurality of skull pin means circumferentially arranged on said ring for attaching said ring to a patient's skull.

3. Apparatus as defined in claim 1, wherein said first connecting means is vertically adjustable relative to said support means.

4. Apparatus as defined in claim 1, wherein said second connecting means includes a corset adapted to be worn by the patient adjacent the lumbar and sacral regions of the patient's spine.

5. Apparatus as defined in claim 4, wherein said second connecting means is vertically adjustable relative to said support means.

6. Apparatus as defined in claim 1, wherein said force-applying means includes:
    (1) a pad; and
    (2) means adjustably connecting said pad with said support means for displacement in a horizontal direction generally normal to said support means, thereby to permit the application of a desired force to the apex of the thoracic spine region of the patient.

7. Apparatus as defined in claim 6, wherein said force-applying means is vertically adjustable relative to said support means.

8. Apparatus as defined in claim 6, wherein said support means includes a pair of spaced parallel vertical rods, and further wherein said adjustable connecting means includes a horizontal bridging member extending between said rods, said bridging member containing a threaded bore, and adjusting screw threadably mounted within said bore and terminating at one end adjacent said pad, and means connecting said one screw end with said pad.

* * * * *